United States Patent [19]

Mochizuki et al.

[11] Patent Number: 5,395,916
[45] Date of Patent: Mar. 7, 1995

[54] BIODEGRADABLE COPOLYMER FROM HYDROXY PROLINE

[75] Inventors: Seiji Mochizuki, Hino; Kiyoshi Nawata, Hachioji; Yuji Makino; Yoshiki Suzuki, both of Hino, all of Japan

[73] Assignee: Teijin Limited, Osaka, Japan

[21] Appl. No.: 62,335

[22] Filed: May 17, 1993

Related U.S. Application Data

[63] Continuation of Ser. No. 937,674, Sep. 1, 1992, abandoned.

[30] Foreign Application Priority Data

Sep. 6, 1991 [JP] Japan .................. 3-254290

[51] Int. Cl.$^6$ .............................................. C08G 69/10
[52] U.S. Cl. .................................. 528/327; 528/328; 528/354; 528/361
[58] Field of Search .............. 528/327, 328, 354, 361

[56] References Cited

U.S. PATENT DOCUMENTS

| | | | |
|---|---|---|---|
| Re. 30,170 | 12/1979 | Goodman et al. | 528/328 |
| 4,093,709 | 6/1978 | Choi et al. | 424/19 |
| 4,831,107 | 5/1989 | Erhan | 528/328 |

FOREIGN PATENT DOCUMENTS

| | | |
|---|---|---|
| 0467389A2 | 1/1992 | European Pat. Off. . |
| 58-140022 | 8/1983 | Japan . |
| 61-172813A | 8/1986 | Japan . |
| 62-201816 | 5/1987 | Japan . |
| 63-41416A | 2/1988 | Japan . |
| 1216917A | 8/1989 | Japan . |

OTHER PUBLICATIONS

Kimura, Kitao and Shirotani: "Kobunshi Kakoh (i.e., Macromolecule Processing)" 37(7), 327–334, 1988.
A. J. Domb and R. Langer, "Polyanhydrides. I. Preparation of High Molecular Weight Polyanhydrides", *Journal of Polymer Science: Part A: Polymer Chemistry*, vol. 25, 3373–3386 (1987).
T. Heya, H. Okada, and Y. Tanigawara, "Effects of TRN and Loading amount on control of TRN release from copoly(dl–lactic/glycolic acid) microspheres prepared by an in water drying method", *International Journal of Pharmaceutics*, 69 (1991) 69–75.
J. Kohn, "Pseudopoly(amino acids)", in *Biodegradable Polymer as Drug Delivery System (1990)*, pp. 195–229.
Heewon Yu Kwon and Robert Langer, "Pseudopoly(amino acids): A Study of the Synthesis and Characterization of Poly(trans–4–hydroxy-N–acyl-L–proline esters)", *Macromolecules*, 1989, 22, 3250–3255.

(List continued on next page.)

*Primary Examiner*—John Kight, III
*Assistant Examiner*—Shelley A. Dodson
*Attorney, Agent, or Firm*—Sughrue, Mion, Zinn, Macpeak & Seas

[57] ABSTRACT

A biodegradable copolymer having the constituent units represented by the structures (I) and (II):

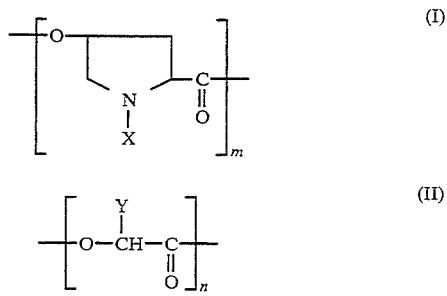

wherein X represents a hydrogen atom, an acyl group having the formula RCO— where R is a hydrocarbon group having 1 to 20 carbon atoms, an alkoxy group having to 20 carbon atoms, and Y represents a hydrogen atom or an alkyl group having 1 to 8 carbon atoms, and m and n are independently integers of 1 or more, m+n is at least 10, and m/(m+n) is at least 0.01 and a pharmaceutical composition containing the same.

4 Claims, 1 Drawing Sheet

OTHER PUBLICATIONS

Andres Staubli, Eyal Ron and Robert Langer, "Hydrolytically Degradable Amino Acid Containing Polymers", *J. Am. Chem. Soc.*, 1990, 112, 4419–4424.

J. Kohn and R. Langer, "Polymerization Reactions Involving the Side Chain of α-L-Amino Acids", *J. Am. Chem. Soc.*, 1987, 109, 817–820.

Kwon et al., "Pseudopoly(amino acids): A Study of the Synthesis and Characterization of Poly(trans-4-hydroxy-N-acyl-L-proline esters)", *Macromolecules*, vol. 22, No. 8, (1989) pp. 3250–3255.

Patent Abstracts of Japan, vol. 012, No. 252 (C-512), Jul. 15, 1988; & JP-A-63 041 416 (Takeda Chem. Ind. Ltd.) Feb. 22, 1988.

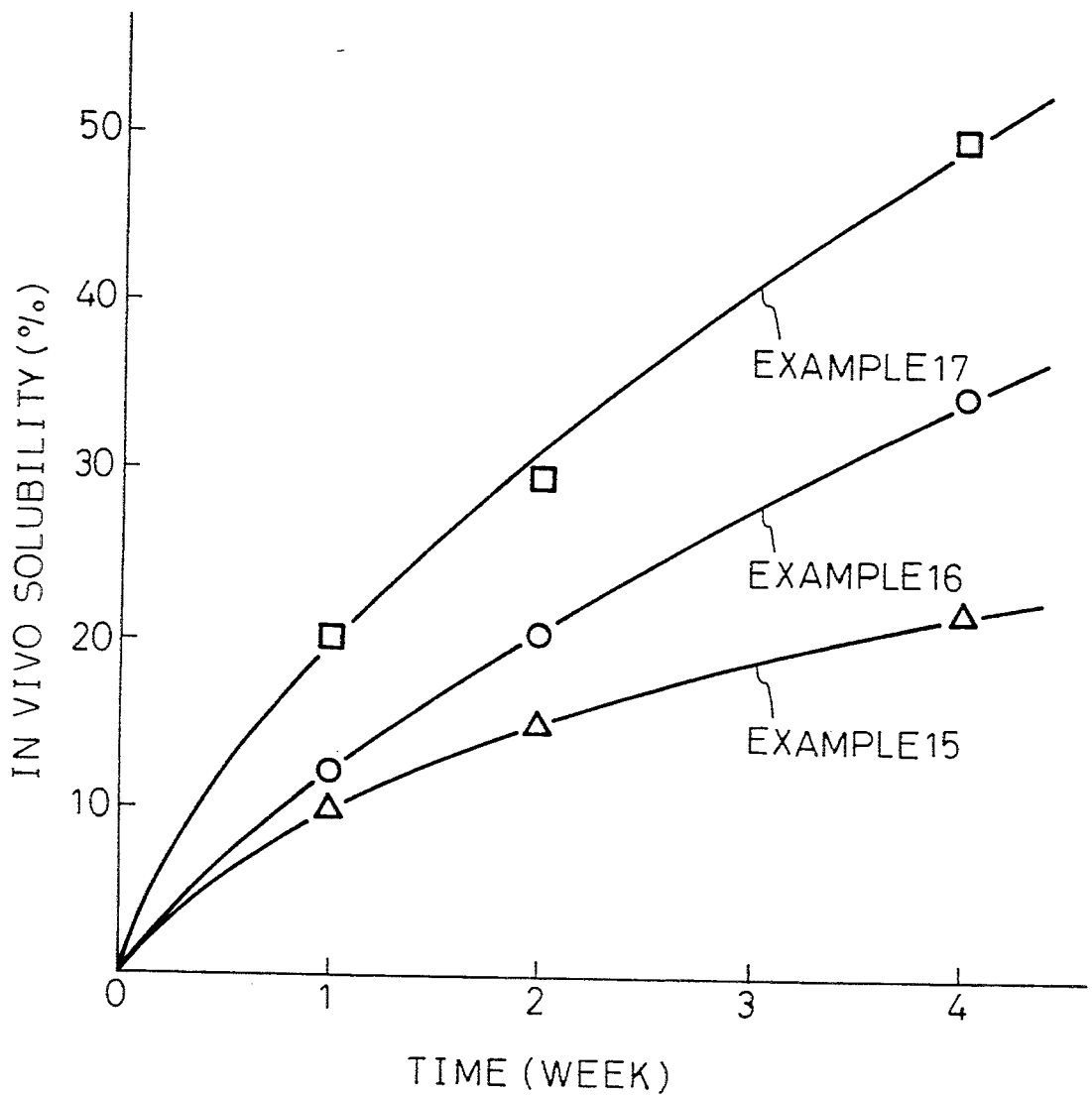

BIODEGRADABLE COPOLYMER FROM HYDROXY PROLINE

This is a continuation of application Ser. No. 07/937,674, filed Sep. 1, 1992, now abandoned.

BACKGROUND OF THE INVENTION

1. Field of the Invention

The present invention relates to a biodegradable copolymer. More specifically, the present invention relates to a biodegradable copolymer having trans-4-hydroxy-L-proline or its N-substituted derivative as one of its constituent units. The present invention also relates to a pharmaceutical composition comprising this copolymer and a therapeutically effective amount of drug.

2. Description of the Related Art

Numerous drugs have been discovered in the past either by synthesis or extraction from natural substances and so forth. These drugs are used as therapeutic drugs by being injected into the body (i.e., bodies of humans or animals) or orally administered, etc. However, even if these drugs are administered into the body, there are many cases in which they do not demonstrate the anticipated physiological activity. This is due to the facts that the drugs are, for example, inadequately absorbed from the digestive tract, the drugs are digested or excreted, the drugs have extremely poor stability in the blood even if they enter the blood, the drugs are immediately decomposed so that they do not reach the site of action where they are to demonstrate their physiological activity, or they are in an inadequate amount even if they reach that site. Thus, in order to demonstrate the maximum physiological activity of the drug so that it functions as a therapeutic drug that is beneficial to the body, it is necessary to optimize the amount of drug at the site of action as well as that timing by controlling the kinetics of the drug in the body, including absorption, distribution, metabolism and excretion. This type of technology is typically referred to as a drug delivery system (DDS).

Although there are various means of controlling the kinetics of drugs in the body as mentioned above, these can be broadly divided into two methods. The first method involves chemical modification of the drug itself. The second method involves forming a composition containing the unchanged drug and another substance, more specifically, a carrier, to control the kinetics of the drug dependent on this carrier.

Although the former method is effective and is used practically being referred to as a prodrug, as the drug itself is chemically modified, it is structurally different from the original drug. On the other hand, in the case of the latter method, as the drug itself is not changed in any manner, the system is simpler than the former method with respect to the form of the drug, which is identical to the original drug. Accordingly, this method has been attempted using many carriers.

Examples of such a carrier include molecular aggregates of molecules such as liposome, and macromolecules such as poly(lactic acid), poly(glycolic acid), phospholipid, albumin, gelatin and collagen. Particularly, extensive research has been conducted in the past with respect to macromolecules, and there are many examples of their practical use in various forms (see, for example, "Biodegradable Polymers as Drug Delivery Systems", M. Chastin and R. Langer ed., Marcel Dekker pub., 1990).

Pharmaceutical compositions comprising this type of drug and carrier are administered into the body for various purposes, in various forms and in various manners.

For example, in order to gradually release a drug having either systemic or localized action, after containing the drug in a carrier using a suitable method, the drug-containing carrier is formed into microparticles having a diameter of several tens of microns and injected either subcutaneously or intramuscularly. A given amount of the drug is then gradually released from the microparticles at the injection site so as to maintain the concentration of drug in the body constant for an extended period of time (normally within a range of about one week or more up to about one year). Alternatively, similar microgranules are injected into a joint so as to maintain the concentration of drug in the joint at a constant high level for an extended period of time.

In addition, after incorporating the drug in the carrier using a suitable method, the drug-containing carrier is formed into a pellet having a size of several millimeters or more, followed by subcutaneous or intramuscular administration by making an incision. After suturing the incision, a given amount of the drug is released from the pellet for an extended period of time, after which an incision is again made and the pellet is removed.

Moreover, other methods include the preparation of an oral vaccine by oral administration of the above-mentioned microparticles, followed by the uptake of said microparticles by mesenteric lymph tissue resulting in an immunological reaction for the purpose of vaccination. In addition, another method involves the preparation of a vaccine by nasal administration of similar microgranules followed by the uptake of said microgranules by respiratory lymph tissue.

In order for pharmaceutical compositions used for the purposes and by the methods described above to become effective and safe therapeutic drugs, the carrier itself is required to have the following properties:

(1) The carrier must be a substance having low toxicity and high biocompatibility that does not cause harmful reactions such as inflammations in the body when brought in contact with body tissue.

(2) The carrier must be able to control the release of drug from the pharmaceutical composition.

(3) It is desirable that the carrier itself be biodegradable so that it breaks down in the body and eliminated naturally.

(4) The degradation products of the carrier must also have low toxicity.

(5) The carrier must be able to be easily formed into a form suitable for administration to the body, and the formed product must have suitable mechanical strength for use as a pharmaceutical preparation and so forth.

Although numerous compounds have been synthesized and extracted from naturally occurring substances and attempted to be used as carriers having the above-mentioned properties, the majority of research has been conducted on poly(lactic acid), poly(glycolic acid) and poly(lactic-co-glycolic)acid. These substances are attracting considerable attention as the substances themselves are already being used as suture thread, and their safety has been verified.

As mentioned above, although poly(lactic acid), poly(glycolic acid) and poly(lactic-co-glycolic)acid are already being partially used practically as carriers of microgranular injection preparations functioning as biodegradable polymers, the properties of those carriers are not always satisfactory.

For example, as poly(lactic acid) and poly(glycolic acid) have a high degree of crystallinity and are non-water-soluble, they have a slow rate of hydrolysis, and it is also difficult to control the rate of that hydrolysis. In fact, in the case of administering pharmaceutical compositions of their polymers and drugs, for example, subcutaneously, the situation occurs in which only the polymer remains for an extended period of time at the administration site even after the drug has been released from said composition (Kimura, Kitao and Shirotani: "Kobunshi Kakoh (i.e., Macromolecule Processing)", 37(7), 327–334, 1988).

Several solutions have been proposed with respect to these problems. For example, a method has been proposed wherein polylactic acid is made easily degradable by forming it into a low molecular weight molecule having a molecular weight of about 2,000 (Japanese Unexamined Patent Publication No. 61-172813). However, this method has been indicated to have problems including poor moldability and difficulty in forming microparticles (or microcapsules).

On the other hand, poly(lactic-co-glycolic)acid have a low degree of crystal formation by virtue of their structure being that of a copolymer. As a result, the problems accompanied with the above-mentioned polylactic acid and polyglycolic acid are solved since the rate of hydrolysis is greater in comparison to that of said lactic acid and glycolic acid. However, when this copolymer is used as a drug carrier, although the completion of drug release and the elimination of the carrier can be coincided, a relatively large amount of drug is released initially (referred to as the "initial burst phenomenon"), after which the release rate decreases, whereby a continuous and effective constant release of drug into the body cannot be effected. It is known that this phenomenon is particularly remarkable in the case where the drug is a hydrophilic, water-soluble drug such as a peptide or protein (Japanese Unexamined Patent Publication No. 1-216917).

This initial burst phenomenon has an extremely significant effect on the body when the drug in question possesses considerable physiological activity. In other words, the greater the physiological activity of the drug, the more important it is to carefully control its concentration within the therapeutically effective range. Thus, methods for suppressing this initial burst phenomenon have been proposed not only for the above-mentioned poly(lactic-co-glycolic)acid, but also for numerous other biodegradable carriers.

For example, although Langer et al. proposed a biodegradable carrier having a constant release rate, or in other words, zero-order release, using polyanhydride (Journal of Polymer Science Part A, Vol. 25, 3373 (1987)), it has been indicated to have numerous problems that have prevented its practical use, including being difficult to handle due to its remarkably high solubility in water, it being unable to release the drug at a constant rate over a period of time of 1 month or more, and it being difficult to form into microcapsules due to its low mechanical strength.

In addition, although Choi et al. have proposed a biodegradable carrier having a constant release rate using polyorthoester (U.S. Pat. No. 4,093,709), it also has been indicated to have problems that prevented its practical use, including the requiring of an additive for control of the rate of hydrolysis, and it being unable to achieve zero-order release when the physiologically active substance is hydrophilic.

Moreover, although efforts have also been made in the past to use biomacromolecules such as collagen, gelatin and albumin as biodegradable carriers having zero-order release, these substances have been indicated to have problems such as the formation of antigenicity and difficulty in forming microcapsules.

In addition, although these methods have resulted in the proposal of carriers having new structures in order to suppress the above-mentioned initial burst phenomenon, there have also been proposals made stating that these problems can be solved even by using conventional lactic-acid-glycolic acid copolymers as is.

For example, a method has been reported, wherein zero-order release is possible by using gelatin gel for the internal aqueous phase when manufacturing microcapsules consisting of drug and a poly(lactic-co-glycolic)acid using immersion drying (Japanese Unexamined Patent Publication No. 62-201816). However, those drugs capable of achieving zero-order release with this method are said to be only LH-RH substances (Ogawa, et al.: International Journal or Pharmaceutics, 69, 69–75 (1991)), and as such, cannot be said to be a universal method that can be applied for numerous drugs. In addition, although a method for manufacturing a composition consisting of a drug derivative and poly(lactic-co-glycolic)acid has been reported in order to increase the interaction between the drug and the carrier (Japanese Unexamined Patent Publication No. 63-41416), this method is also not a universal method that can be applied to numerous drugs.

Thus, there is a need for a universal material that can be manufactured into a carrier that has a high degree of biocompatibility, is biodegradable, allows control of drug release by suppressing initial burst phenomenon in particular, can be formed into various types of administration forms, and allows the resulting formed product to have adequate mechanical strength. In particular, there is a need for poly(lactic acids), poly(glycolic acids) and poly(lactic-co-glycolic)acid that suppress initial burst phenomenon and allow control of drug release.

SUMMARY OF THE INVENTION

Accordingly, the objects of the present invention are to eliminate the above-mentioned disadvantageous of the conventional art and to provide a biodegradable and biocompatible polymer capable of controlling drug release by suppressing initial burst phenomenon and also capable of being formed into various types of administration forms having adequate mechanical strength.

Other objects and advantages of the present invention will be apparent from the following description.

In accordance with the present invention, there is provided a biodegradable copolymer having the constituent units represented by the structures (I) and (II);

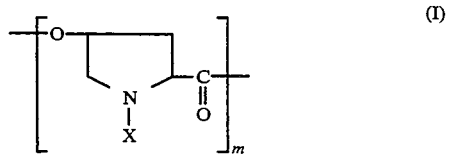

-continued

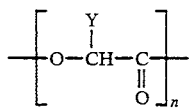
(II)

wherein X represents a hydrogen atom, an acyl group having the formula RCO— where R is a hydrocarbon group having 1 to 20 carbon atoms, an alkoxy group having 1 to 20 carbon atoms, and Y represents a hydrogen atom or an alkyl group having 1 to 8 carbon atoms, and m and n are independently integers of 1 or more, m+n is at least 10, and m/(m+n) is at least 0.01.

In accordance with the present invention, there is also provided a pharmaceutical composition comprising the above-mentioned copolymer and a therapeutically effective amount of a drug.

BRIEF DESCRIPTION OF THE DRAWINGS

The present invention will be better understood from the description set forth below with reference to the accompanying drawing of FIG. 1, which illustrates the in vivo solubility of the copolymers of the present invention in Example 21.

DESCRIPTION OF THE PREFERRED EMBODIMENTS

As a result of earnest efforts by the inventors of the present invention to solve the above-mentioned problems, it was found that the copolymer having the constituent units represented in the structures [I] and [II] is able to solve the above-mentioned problems, and thus, the present invention is completed.

Poly-[N-acyl-trans-4-hydroxy-L-proline], represented by the formula (III), has previously been reported by Langer et al. (Macromolecules 22, 3250–3255 (1989)).

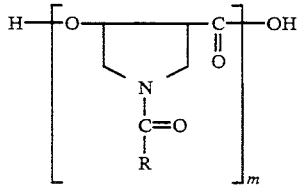
(III)

According to the above reference, a polymer product is reported wherein the R(C=O)— portion of formula (III) represents palmitoyl, tetradecanoyl, decanoyl, hexanoyl, pivaloyl or acetyl, and m=about 9–41. In addition, it is described that such a poly-(N-acyl-trans-4-hydroxy-L-proline) is biodegradable, can be formed into a pharmaceutical composition by forming, for example, into microcapsules with a drug, that is used as the material for a drug delivery system. Although there is not much described concerning its properties, it is described that poly-(N-palmitoyl-trans-4-hydroxy-L-proline) is largely hydrophobic, and its rate of hydrolysis is slower than polylactic acid. As the trans-4-hydroxy-L-proline that composes this homopolymer is a naturally-occurring amino acid, and in particular, is a primary component of collagen which comprises connective tissue, it is expected to function as a carrier of pharmaceutical compositions for subcutaneous or intramuscular injection preparations. However, it is difficult to use this homopolymer as is as a carrier of pharmaceutical compositions. In addition, methods of improving conventional poly-(N-acyl-trans-4-hydroxy-L-proline), such as poly-(N-palmitoyl-trans-4-hydroxy-L-proline), so as to give it properties that are desirable for use as a carrier of pharmaceutical compositions are not proposed. What is more, not only is there no description of lactic acid, glycolic acid or poly(lactic-co-glycolic)acid, there is not even any suggestion of such.

Furthermore, the suggestion of the formation of poly-(N-benzyloxycarbonyl-trans-4-hydroxy-L-proline) represented by the formula (IV);

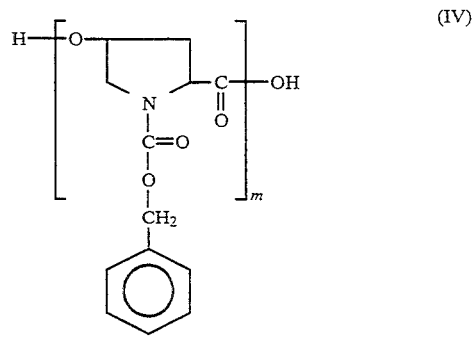
(IV)

is described although its formation by actual synthesis is not reported (Biodegradable polymer as Drug Delivery System; M. Chasin, R. Langer, ed., Marcel Dekker pub., 1990, p. 202). However, the degradation properties of this polymer are not reported, and the copolymer of lactic acid and/or glycolic acid, is neither disclosed nor taught in this reference.

On the other hand, although a polymer of cis-4-hydroxy-L-proline is reported to be a composition that suppresses the cellular conjugation of animal collagen fiber (Japanese Unexamined Patent Publication No. 58-140022), details concerning the physical properties of that polymer are unclear, and there is not even any suggestion of a copolymer of lactic acid and/or glycolic acid.

Thus, it can be understood that the compound of the present invention is a new analogue of poly(lactic acid), poly(glycolic acid) or a poly(lactic-co-glycolic)acid, while also being a new analogue of poly-N-substituted-hydroxyproline.

In addition, the present invention also provides a pharmaceutical composition comprising a copolymer having the constituent units represented by the above-mentioned structures (I) and (II), and a therapeutically effective amount of a drug.

Moreover, the present invention also provides a pharmaceutical composition in the form of a microgranular formed product and preferably having an average diameter of 0.01 to 400 μm, more preferably 0.05 to 200 μm, comprising a copolymer having the constituent units represented by the above-mentioned structures (I) and (II), and a therapeutically effective amount of a drug.

Furthermore, the present invention also provides a pharmaceutical composition in the form for injection, oral or nasal administration, that is a microparticles formed product preferably having an average diameter of 0.01 to 400 μm, more preferably 0.05 to 200 μm, and comprising a copolymer having the constituent units represented by the above-mentioned structure (I) and (II), and a therapeutically effective amount of a drug.

In the present invention, X represents a hydrogen atom or an acyl group represented by RCO in the above-mentioned structure (I). Examples of R of the acyl group of the present invention include hydrocarbon groups having 1–20 carbon atoms including an alkyl group having 1 to 20 carbon atoms, preferably 4 to 18 carbon atoms, an alkenyl group having 2 to 20 carbon atoms more preferably 4 to 18 carbon atoms, and an aromatic group having 6 to 10 carbon atoms, preferably 6 to 8 carbon atoms. Examples of acyl groups resulting from these hydrocarbon groups include aliphatic or aromatic acyl groups such as acetyl, propionyl, butyryl, pentanoyl, pivaloyl, hexanoyl, heptanoyl, octanoyl, decanoyl, tetradecanoyl and palmitoyl oleoyl, linoleoyl, linolenoyl groups, benzoyl and toluoyl groups, as well as groups wherein these carbon atoms are substituted by other substitution groups. Examples of other substitution groups include carboxy groups such that the acyl group becomes a succinyl group, glutaryl group, adipinyl group or cebacyl group, or amide groups such that the acyl group becomes an aminosuccinyl group, aminoglutaryl group, aminoadipinyl group or aminosebacyl group. In particular, an acetyl group, pivaloyl group, hexanoyl group, decanoyl group, tetradecanoyl group or palmitoyl group are preferable for the acyl group.

In addition, examples of R include an aliphatic or aromatic alkoxy group having 1–20 carbon atoms with an aliphatic group having 1 to 20 carbon atoms, preferably 4 to 8 carbon atoms and an aromatic group having 7 to 20 carbon atoms, preferably 7 to 9 carbon atoms, as exemplified as the alkyl groups and the aromatic group in the above R of the acyl group. Examples of such groups include methoxy groups, ethoxy groups, (n- or i-) propoxy groups, (n-, sec- or t-) butoxy groups, pentoxy groups and benzyloxy, phenethyloxy, trityloxy groups as well as groups wherein these carbon atoms are substituted by other substitution groups, as exemplified above. There are no limitations on these substitution groups as long as they are able to provide a copolymer having the desired properties of the present invention, such as biodegradability. Particularly, t-butoxy and benzyloxy groups are especially preferable for R.

In addition, in the copolymer of the present invention, the case wherein X is both a hydrogen atom and an acyl group represented by RCO— in the above-mentioned structure (I), which is a constituent unit of the present invention, is also an embodiment of the present invention.

In the present invention, X is preferably a hydrogen atom, palmitoyl group, tetradecanoyl group, decanoyl group, hexanoyl group, pivaloyl group, acetyl group, t-butoxycarbonyl group or benzyloxycarbonyl group.

In the case the above-mentioned X in the constituent unit represented by the structure (I) of the present invention is a hydrogen atom, this will be hereinafter referred to as trans-4-hydroxy-L-proline, and in the case X is an acyl group, this will be hereinafter referred to as an N-substituted derivative of trans-4-hydroxy-L-proline.

In addition, Y represents a hydrogen atom or alkyl group by the above-mentioned structure (II). Although there is no particular limitation on Y as long as it provides a copolymer that has the desired properties of the present invention, such as biodegradability, examples of Y include linear or cyclic alkyl groups such as a methyl group, ethyl group, (n- or i-)propyl group, (n-, sec- or t-)butyl group, pentyl group and hexyl group, with a methyl group being particularly preferable for the alkyl group. In the case where Y is a hydrogen atom in the structure (II), the structure (II) represents glycolic acid, and in the case where Y is a methyl group, the structure (II) represents lactic acid. In addition, in the copolymer of the present invention, the case wherein Y is both a hydrogen atom and a methyl group in the above-mentioned structure (II), which is a constituent unit of the present invention, is also an embodiment of the present invention. In the case Y is a hydrogen atom and a methyl group, the structure (II) represents glycolic acid and lactic acid.

In addition, in the above-mentioned structures (I) and (II), m and n are integers of 1 or more, m+n is at least 10 and m/(m+n) is at least 0.01. As long as m and n satisfy the above, a copolymer having constituent units of the above-mentioned structures (I) and (II) are included in the embodiment of the present invention, whether it be a block copolymer or a random copolymer. The preferable copolymer is a random copolymer.

In the copolymer of the present invention, the polymerization ratio of the trans-4-hydroxy-L-proline and the constituent unit represented in the above-mentioned formula [I] is preferably about 1:99 to 50:50, and more preferably roughly 5:95 to 35:65. In addition, an example of the molecular weight of the copolymer of the present invention is typically about 1,000 to 40,000, more preferably 2,000 to 20,000.

The following provides an explanation of the copolymer of the present invention using trans-4-hydroxy-L-proline derivatives for the constituent unit represented in the above-mentioned structure (I), and lactic acid and/or glycolic acid for the constituent unit represented by the above-mentioned formula (II).

Preferable examples of the copolymer of the present invention include trans-4-hydroxy-L-proline/lactic acid copolymer, trans-4-hydroxy-L-proline/glycolic acid copolymer, and trans-4-hydroxy-L-proline/lactic acid/glycolic acid copolymer. In the case of copolymers of N-acyl-trans-4-hydroxy-L-proline and lactic acid and/or glycolic acid, preferable examples of the copolymer of the present invention include copolymers wherein the above-mentioned acyl group is substituted, such as N-palmitoyl-trans-4-hydroxy-L-proline/lactic acid copolymer, N-palmitoyl-trans-4-hydroxy-L-proline/glycolic acid copolymer, N-palmitoyl-trans-4-hydroxy-L-proline/lactic acid/glycolic acid copolymer, N-tetradecanoyl-trans-4-hydroxy-L-proline/lactic acid copolymer, N-tetradecanoyl-trans-4-hydroxy-L-proline/glycolic acid copolymer, N-tetradecanoyl-trans-4-hydroxy-L-proline/lactic acid/glycolic acid copolymer, N-decanoyl-trans-4-hydroxy-L-proline/lactic acid copolymer, N-decanoyl-trans-4-hydroxy-L-proline/glycolic acid copolymer, N-decanoyl-trans-4-hydroxy-L-proline/lactic acid/glycolic acid copolymer, N-benzyloxycarbonyl-trans-4-hydroxy-L-proline/lactic acid copolymer, N-benzyloxycarbonyl-trans-4-hydroxy-L-proline/glycolic acid copolymer and N-benzyloxycarbonyl-trans-4-hydroxy-L-proline/lactic acid/glycolic acid copolymer, if the acyl group is a palmitoyl group, tetradecanoyl group or decanoyl group.

The copolymer of the present invention is produced can be produced by using, for example, the following method.

An explanation is first provided regarding the production of trans-4-hydroxy-L-proline/lactic acid copolymer represented by formula (V) below:

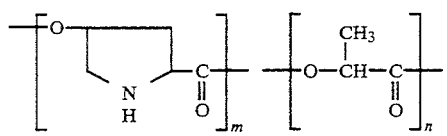

(V)

A polyester is synthesized using trans-4-hydroxy-L-proline and lactic acid as the starting materials. The reaction in this case involves stirring the starting materials for usually 10–50 hours under reduced pressure (5 Torr or less) while maintaining the temperature at about 180° C. using resin (e.g., ion exchange resin) for the catalyst. Following completion of the reaction, the reaction product is dissolved in an organic solvent such as methylene chloride. Following filtration, the solution is reprecipitated with a poor solvent such as n-hexane followed by separation of the formed copolymer. Although the blended ratio of trans-4-hydroxy-L-proline and lactic acid (mole ratio, to be treated similarly hereinafter) is typically within a range of about 1:99 to 50:50, a more preferable range is 5:95 to 30:70. Although the degree of polymerization is influenced by reaction temperature, polymerization time, catalyst and polymerization ratio, the degree of polymerization is typically 10–200, and the molecular weight (weight average molecular weight, to be treated similarly hereinafter) is typically roughly 1,000 to 40,000.

In addition, the trans-4-hydroxy-L-proline/lactic acid copolymer of formula (V) is synthesized by carrying out a molten ester exchange reaction using poly(lactic acid) and trans-4-hydroxy-L-proline for the starting materials.

The reaction in this case involves stirring polyglycolic acid having a molecular weight of about 2,000 to 100,000 and trans-4-hydroxy-L-proline for generally 30 minutes to 12 hours under reduced pressure (e.g., 5 Torr or less) while maintaining the temperature at about 160° C. Following completion of the reaction, the reaction product is dissolved in an organic solvent such as methylene chloride. Following filtration, the solution is reprecipitated with a solvent such as n-hexane followed by separation of the formed copolymer. In addition, the trans-4-hydroxy-L-proline/lactic acid copolymer represented in formula [V] is synthesized by first synthesizing an N-benzyloxycarbonyl-trans-4-hydroxy-L-proline/lactic acid copolymer to be subsequently described.

This is followed by elimination of the benzyloxycarbonyl group represented in reaction formula [VI] indicated below by contact hydrogenation.

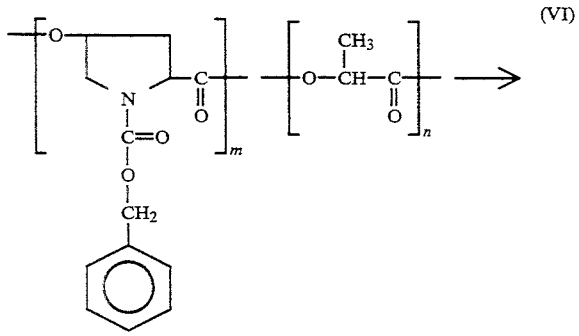

(VI)

-continued

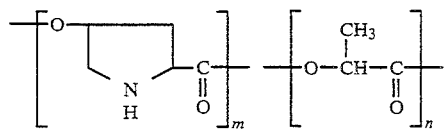

In this case, the benzyloxycarbonyl group elimination reaction of the N-benzyloxycarbonyl-trans-4-hydroxy-L-proline/lactic acid copolymer involves dispersing said copolymer in a mixture of acetic acid and ethanol, wherein (the mixing ratio of acetic acid to ethanol is preferably within a range of 50:50 to 20:80 using Pd/C (palladium/carbon) for the catalyst, and stirring for 2–24 hours in the presence of $H_2$. Following completion of the reaction, the Pd/C catalyst is removed by filtering, followed by reprecipitation with n-hexane and separation of the formed copolymer.

Although the mixing ratio of trans-4-hydroxy-L-proline or N-benzyloxycarbonyl-trans-4-hydroxy-L-proline and lactic acid is typically about 1:99 to 50:50, it is more preferably within a range of about 5:95 to 30:70. Although the degree of polymerization is influenced by the reaction temperature, the charged mole ratio and so forth, it is typically 10–200, and the molecular weight is about 1,000–40,000.

The following describes the method for producing N-acyl-trans-4-hydroxy-L-proline/lactic acid copolymer indicated by formula [VII] below.

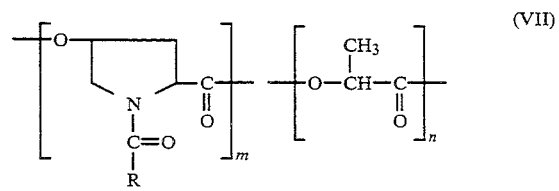

(VII)

First of all, trans-4-hydroxy-l-acyl-L-proline methyl ester is synthesized according to the method of Langer, et al. (Macromolecules, 22, 3250–3255 (1989)). Ester is eliminated from the resulting produced with alkali (KOH or NaOH) to obtain trans-4-hydroxy-l-acyl-L-proline. Moreover, a polyester is then synthesized using said compound and lactic acid. The reaction in this case involves stirring for about 10–80 hours under reduced pressure (e.g., 5 Torr or less) while maintaining the temperature at about 180° C. using resin (i.e., ion exchange resin) for the catalyst. Following completion of the reaction, the reaction product is dissolved in an organic solvent such as methylene chloride. Following filtration, the solution is reprecipitated with a poor solvent such as n-hexane followed by separation of the formed copolymer.

Although the mixing ratio of trans-4-hydroxy-l-acyl-L-proline and lactic acid is typically about 1:99 to 50:50, it is more preferably within a range of about 5:95 to 30:70. Although the degree of polymerization is influenced by the reaction temperature, polymerization time, catalyst and polymerization ratio, it is typically about 10–200, and the molecular weight is typically about 500–20,000.

In addition, the N-acyl-trans-4-hydroxy-L-proline/lactic acid copolymer represented by the formula (VII) is also synthesized by carrying out transesterification using poly(lactic acid) and trans-4-hydroxy-1-acyl-L-proline as the starting materials.

The reaction in this case involves stirring polylactic acid preferably having a molecular weight of about 2,000–100,000 and trans-4-hydroxy-1-acyl-L-proline for generally 30 minutes to 12 hours under reduced pressure (e.g., 5 Torr or less) while maintaining the temperature at about 160° C. Following completion of the reaction, the product is dissolved in an organic solvent such as methylene chloride. After filtration, the solution is reprecipitated with a poor solvent such as n-hexane followed by separation of the formed copolymer.

Although the mixing ratio of trans-4-hydroxy-1-acyl-L-proline and lactic acid is typically about 1:99 to 50:50, it is more preferably within a range of about 5:95 to 30:70. Although the degree of polymerization is influenced by the reaction time, reaction temperature, charged mole ratio and so forth, it is typically about 10–200, and the molecular weight is typically about 1,000–40,000.

The following describes the method for producing N-benzyloxycarbonyl-trans-4-hydroxy-L-proline/lactic acid copolymer indicated by the formula (VIII) below.

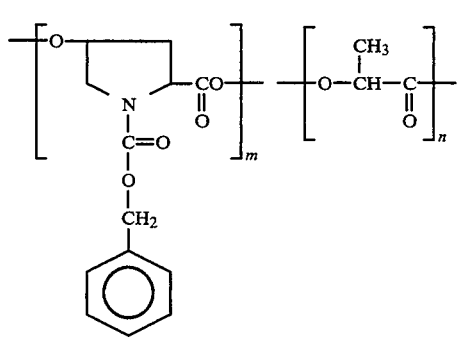

(VIII)

This is obtained by synthesizing a polyester using N-benzyloxycarbonyl-trans-4-hydroxy-L-proline and lactic acid.

The reaction in this case involves stirring for typically 10–80 hours under reduced pressure (e.g., 5 Torr or less) while maintaining the temperature at about 180° C. using resin (i.e., ion exchange resin) for the catalyst. Following completion of the reaction, the reaction product is dissolved in an organic solvent such as methylene chloride. Following filtration, the solution is reprecipitated with a poor solvent such as n-hexane followed by separation of the formed copolymer.

Although the mixing ratio of N-benzyloxycarbonyl-trans-4-hydroxy-L-proline and lactic acid is typically about 1:99 to 50:50, it is more preferably within a range of about 5:95 to 30:70. Although the degree of polymerization is influenced by the reaction temperature, polymerization time, catalyst and polymerization ratio, it is typically about 10–200, and the molecular weight is typically about 500–20,000.

In addition, the N-benzyloxycarbonyl-trans-4-hydroxy-L-proline/lactic acid copolymer represented in formula [VIII] is also synthesized by carrying out transesterification using poly(lactic acid) and N-benzyloxycarbonyl-trans-4-hydroxy-L-proline as the starting materials.

The reaction in this case involves stirring polylactic acid preferably having a molecular weight of about 2,000–100,000) and N-benzyloxycarbonyl-trans-4-hydroxy-L-proline for generally 30 minutes to 12 hours under reduced pressure (e.g., 5 Torr or less) while maintaining the temperature at about 160° C. Following completion of the reaction, the product is dissolved in an organic solvent such as methylene chloride. After filtration, the solution is reprecipitated with a poor solvent such as n-hexane followed by separation of the formed copolymer.

Although the mixing ratio of N-benzyloxycarbonyl-trans-4-hydroxy-L-proline and lactic acid is typically about 1:99 to 50:50, it is more preferably within a range of about 5:95 to 30:70. Although the degree of polymerization is influenced by the reaction time, reaction temperature, charged mole ratio and so forth, it is typically roughly 10–200, and the molecular weight is typically about 1,000–40,000.

The following explains the method for producing the trans-4-hydroxy-L-proline/glycolic acid copolymers represented by the formulae (IX), (X) and (XI) below, wherein the lactic acid portions of the trans-4-hydroxy-L-proline/lactic acid polymers represented by the above-mentioned formulae (V), (VII) and (VIII) are substituted with glycolic acid.

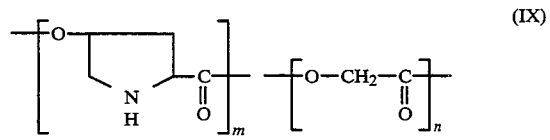

(IX)

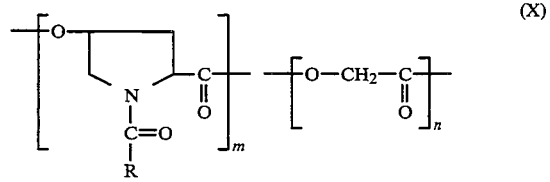

(X)

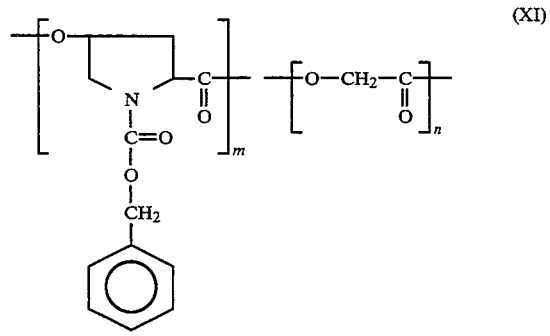

(XI)

In general, although these syntheses should be performed by using glycolic acid in place of the lactic acid used in the sections describing the synthesis methods of the above-mentioned formulae (V), (VII) and (VIII), the following provides a more detailed explanation of those syntheses.

Synthesis is performed by first synthesizing a polyester using trans-4-hydroxy-L-proline and glycolic acid, trans-4-hydroxy-1-acyl-L-proline and glycolic acid, or N-benzyloxycarbonyl-trans-4-hydroxy-L-proline and glycolic acid.

The reaction in this case involves stirring for typically 10–80 hours under reduced pressure (e.g., Torr or less) while maintaining the temperature at 180° C. using resin (i.e., ion exchange resin) for the catalyst. Following completion of the reaction, the reaction product is dissolved in an organic solvent such as methylene chloride. Following filtration, the solution is reprecipitated with a poor solvent such as n-hexane followed by separation of the formed copolymer.

Although the mixing ratio of trans-4-hydroxy-L-proline and glycolic acid, trans-4-hydroxy-1-acyl-L-proline and glycolic acid, or N-benzyloxycarbonyl-trans-4-hydroxy-L-proline and glycolic acid is typically within a range of about 1:99 to 50:50, it is more preferably within a range of about 5:95 to 30:70. Although the degree of polymerization is influenced by the reaction temperature, polymerization time, catalyst and polymerization ratio, it is typically about 10–200, and the molecular weight is typically about 500–20,000.

In addition, the copolymers of formulae (IX), (X) and (XI) are also synthesized by carrying out transesterification using poly(glycolic acid) and trans-4-hydroxy-L-proline, poly(glycolic acid) and trans-4-hydroxy-1-acyl-L-proline, or poly(glycolic acid) and N-benzyloxycarbonyl-trans-4-hydroxy-L-proline as the starting materials.

The reaction in this case involves stirring poly(glycolic acid) preferably having a molecular weight of about 2,000–100,000 and trans-4-hydroxy-L-proline, poly(glycolic acid) and trans-4-hydroxy-1-acyl-L-proline, or poly(glycolic acid) and N-benzyloxycarbonyl-trans-4-hydroxy-L-proline for typically 30 minutes to 12 hours under reduced pressure (e.g., 5 Torr or less). Following completion of the reaction, the product is dissolved in an organic solvent such as methylene chloride. After filtration, the solution is reprecipitated with a poor solvent such as n-hexane followed by separation of the formed copolymer.

Although the mixing ratio of trans-4-hydroxy-L-proline and glycolic acid, trans-4-hydroxy-1-acyl-L-proline and glycolic acid, or N-benzyloxycarbonyl-trans-4-hydroxy-L-proline and glycolic acid is typically within a range of about 1:99 to 50:50, it is more preferably within a range of about 5:95 to 30:70. Although the degree of polymerization is influenced by the reaction time, reaction temperature, charged mole ratio and so forth, it is typically about 10–200, and the molecular weight is typically about 1,000–40,000.

Finally, the following explains the method for producing the trans-4-hydroxy-L-proline/lactic acid/glycolic acid copolymers represented by the formulae (XII), (XIII) and (XIV) below.

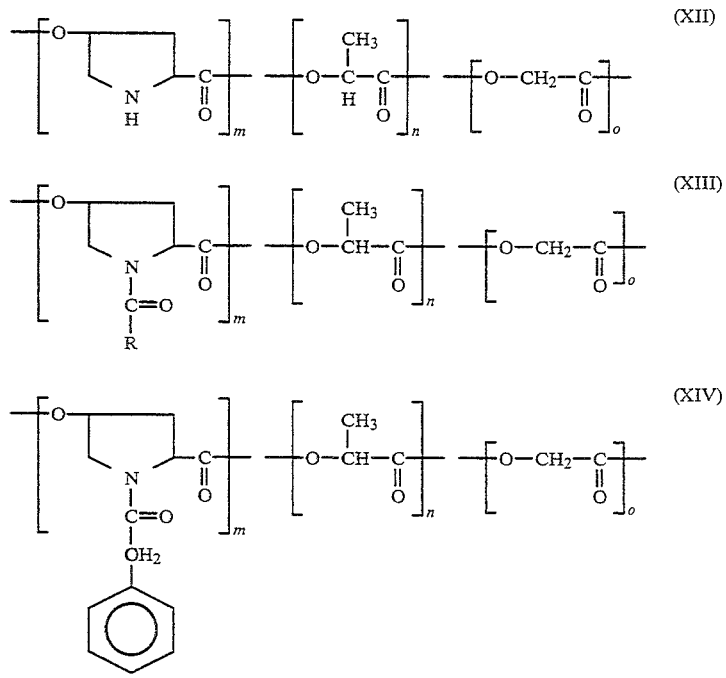

hydroxy-L-proline and glycolic acid is typically within a range of about 1:99 to 50:50, it is more preferably within a range of about 5:95 to 30:70. Although the degree of polymerization is influenced by the reaction temperature, polymerization time, catalyst and polymerization ratio, it is typically about 10–200, and the molecular weight is typically about 500–20,000.

In general, although these syntheses should be performed by using mixtures of lactic acid and glycolic acid in place of the lactic acid used in the sections describing the synthesis methods of the above-mentioned formulae (V), (VII) and (VIII), the following provides a more detailed explanation of those syntheses.

Synthesis is performed by first synthesizing a polyester using trans-4-hydroxy-L-proline, lactic acid and glycolic acid, trans-4-hydroxy-1-acyl-L-proline, lactic acid and glycolic acid, or N-benzyloxycarbonyl-trans-4-hydroxy-L-proline, lactic acid and glycolic acid.

The reaction in this case involves stirring for typically 10–80 hours under reduced pressure (e.g., 5 Torr or less) while maintaining the temperature at about 180° C. using resin (i.e., ion exchange resin) for the catalyst. Following completion of the reaction, the reaction product is dissolved in an organic solvent such as methylene chloride. Following filtration, the solution is reprecipitated with a poor solvent such as n-hexane followed by separation of the formed copolymer.

Although the sum of the polymerization ratio of lactic acid and glycolic acid, and the mixing ratio of trans-4-hydroxy-L-proline, trans-4-hydroxy-1-acyl-L-proline, or N-benzyloxycarbonyl-trans-4-hydroxy-L-proline are typically within a range of about 1:99 to 50:50, they are more preferably within a range of about 5:95 to 30:70. In addition, although the ratio of lactic acid and glycolic acid can be set as desired, a typical ratio of lactic acid in PLGA is preferably 50% or more, with a ratio of 75% or more being particularly preferable. Although the degree of polymerization is influenced by the reaction temperature, polymerization time, catalyst and polymerization ratio, it is typically about 10–200, and the molecular weight is typically about 500–20,000.

In addition, the copolymers of formulae (XII), (XIII) and (XIV) are also synthesized by carrying out transesterification using poly(lactic-co-glycolic)acid (PLGA) and trans-4-hydroxy-L-proline, PLGA and trans-4-hydroxy-1-acyl-L-proline, or PLGA and N-benzyloxycarbonyl-trans-4-hydroxy-L-proline as the starting materials.

The reaction in this case involves stirring PLGA preferably having a molecular weight of about 2,000–100,000 and trans-4-hydroxy-L-proline, PLGA and trans-4-hydroxy-1-acyl-L-proline, or PLGA and N-benzyloxycarbonyl-trans-4-hydroxy-L-proline for typically 30 minutes to 12 hours under reduced pressure (e.g., 5 Torr or less). Following completion of the reaction, the product is dissolved in an organic solvent such as methylene chloride. After filtration, the solution is reprecipitated with a poor solvent such as n-hexane followed by separation of the formed copolymer.

Although the sum of the polymerization ratio of lactic acid and glycolic acid, and the mixing ratio of trans-4-hydroxy-L-proline, trans-4-hydroxy-1-acyl-L-proline, or N-benzyloxycarbonyl-trans-4-hydroxy-L-proline are typically within a range of about 1:99 to 50:50, they are more preferably within a range of about 5:95 to 30:70. In addition, although the ratio of lactic acid and glycolic acid in PLGA can be set as desired, the typical ratio of lactic acid in PLGA is preferably 50% more, with a ratio of 75% or more being particularly preferable. Although the degree of polymerization is influenced by the reaction time, reaction temperature, charged mole ratio and so forth, it is typically about 10–200, and the molecular weight is typically about 1,000–40,000.

There are no particular limitations on the drug that forms the copolymer having the constitutional units represented by the formulae (I) and (II) of the present invention, and the pharmaceutical composition. Examples of such drugs include peptides, proteins and other antibiotics having physiological activity, antitumor agents, antipyrogenic agents, analgesics, antiphlogistics, antitussives, muscle relaxants, antiepileptics, antidieretic agents, antidepressants, antiallergic agents, cardiacs, arrhythmia therapeutic agents, vasodilators, diuretics, diabetes therapeutic agents, anticoagulants, hemostyptics, tuberculostats, hormone agents and narcotic antagonists.

Specific examples include thyroid stimulating hormone (TSH), leuteinizing hormone (LH), LH—RH, LH—RH analogues, follicle stimulating hormone (FSH), vasopressin, vasopressin derivatives (see Desmopressin (Nippon Naibunpi Gakkai Zasshi) (Journal of the Japan Endocrinology Society, Vol. 54, No. 5, pp. 676–691 (1978)), oxytocin, calcitonin, other calcitonins such as 10 calcitonin derivatives, elcatonine, parathyroid hormone, glucagon, gastrin, insulin, somatostatin, somatostatin derivatives, secretin, prolactin, vancreozymin, cholecystokinin, angiotensin, human placental lactogen, human chorionic gonadotropin (HCG), enkephalin, enkaphalin derivatives (see U.S. Pat. No. 4,277,394, and European Unexamined Patent Application 31, 567), endorphin, kyotrophin, interferon (types $\alpha$, $\beta$ and $\gamma$), interleukin (I, II and III), taftocin, thymopoietin, naimocin, thymostimulin, thymic humor factor (THF), serum thymic factor (STF), its derivatives (see U.S. Pat. No. 4,229,438) and other thymic factors (Igaku no Ayumi, Annals of Medicine), Vol. 125, No. 10, pp.335–343 (1983)), tumor necrotic factor (TNF), colony stimulating factor (CSF), motilin, denorphin, bombecine, neurotensin, cellulain, bradykinin, urokinase, asparginase, kallikrein, substance P, nerve growth factor, blood coagulating factors VIII and IX, lysozyme chloride, polymyxin B, colistin, gramicidin, bacitracin, protein synthesis stimulating peptide (U.K. Patent No. 8,232,082), gastric acid secretion inhibitory polypeptide (GIP), vasoactive intestinal polypeptide (VIP), platelet-derived growth factor (PDGF), growth hormone, growth hormone release factor (GRF, somatocrinin), bone morphagenetic protein (BMP), adrenocortical hormones (ACTH), melanocyte stimulating hormone (MSH), thyroid hormone releasing hormone (TRH), its salts and its derivatives, epithelium growth factor (EGF), vaccines including influenza vaccine, cholera vaccine, polio vaccine, pertussis vaccine BCG vaccine, measles vaccine, German measles vaccine and mumps vaccine, as well as monoclonal and polyclonal antibodies such as anti-T cell receptor monoclonal antibody, anti-CD4 antibody, anti-P glycoprotein antibody and anti-TNF monoclonal antibody.

Examples of the above-mentioned antitumor agents include bleomycin hydrochloride, methotrexate, actinomycin D, mitomycin C, vinbrustin hydrochloride, vincristin hydrochloride, daunorubicin hydrochloride, adriamycin, neocarcinostatin, cytosine arabinoside, fluorouracil, tetrahydrofuryl-5-fluorouracil, PSK (crestin:Sankyo-Kureha Chemical) and OK-432 (Picivanil: Chugai Pharm).

In particular, peptides, proteins, antibodies and vaccines that are both water soluble and hydrophilic are preferable. Examples of these include calcitonine, elcatonine, LH—RH, LH—RH analogues, insulin, somatostatin, somatostatin derivatives, growth hormone, prolactin, adrenocortical hormones (ACTH), melanocyte stimulating hormone (MSH), thyroid hormone releasing hormone (TRH), its salts and its derivatives, monoclonal antibodies, influenza vaccine, pertussis vaccine and polio vaccine.

The drug in a therapeutically effective amount of the present invention refers to an amount of drug able to release an amount that is able to demonstrate effectiveness continuously over a period of several weeks to several months in the case of a pharmaceutical composition comprising these drugs and the copolymer of the present invention. This amount is determined according to the type of drug, the period of time over which it is to be continuously released and so forth.

Although the drug in a therapeutically effective amount of the present invention refers to an amount of drug able to release an amount that is able to demonstrate effectiveness continuously for a period of several weeks to several months in the case of using the pharmaceutical composition comprising these drugs and the copolymer of the present invention as a continuous injection preparation, this amount is determined arbitrarily according to the type of drug, the period of time over which it is to be continuously released and so forth. For example, in order to prepare a preparation to be released gradually over the course of about 1 week to about 1 month, it is normally desirable to contain 1 $\mu$g–50 mg per 100 mg of the pharmaceutical composition in the case of using peptides. For example, a preparation that is gradually released over the course of about 1 month can be produced by containing 80 units of elcatonine per 100 mg of the pharmaceutical composition. In addition, a preparation that is gradually released over the course of about 1 month can be produced by containing 16 $\mu$g of salmon calcitonin per 100 mg of the pharmaceutical composition. In addition, a preparation that is gradually released over the course of about 1 month can be produced by containing 3.6–7.2 mg of leuprolide (LH—RH analogue) per 100 mg of the pharmaceutical composition. In addition, a preparation that is gradually released over the course of about 1 week can be produced by containing 1.1–28 mg of insulin per 100 mg of the pharmaceutical composition. Moreover, a preparation that is gradually released over the course of about 2 weeks can be produced by containing 7–28 mg of TRH per 100 mg of the pharmaceutical composition.

In addition, in the case of using said pharmaceutical composition as an oral or nasal preparation, the amount of said composition refers to the amount by which effects are demonstrated within several doses of said pharmaceutical composition. For example, in the case of an oral or nasal vaccine preparation, it is desirable to contain about 0.1 μg–20 mg per 100 mg of the pharmaceutical composition. For example, an oral or nasal pertussis vaccine preparation is obtained by containing 5 mg per 100 mg of the pharmaceutical composition.

A pharmaceutical composition having various forms can be formed from the copolymer of the present invention and a drug by known methods. Examples of said pharmaceutical composition include formed products such as microcapsules (microparticles), granules, pellets or tablets. The size of these formed products is preferably such that the average diameter is 0.01–400 μm in the case of microcapsules and granules. An average diameter of 2–100 μm is preferable in the case of an administration form for injection, and an average diameter of 0.05–10 μm is preferable in the case of an administration form for oral or nasal administration.

For example, N-palmitoyl-trans-4-hydroxy-L-proline/lactic acid copolymer and a drug can be formed into microcapsules using the method described below. First of all, either N-palmitoyl-trans-4-hydroxy-L-proline/lactic acid copolymer is dissolved in an organic solvent such as methylene chloride, or the drug is added followed by dissolving or dispersion. The solution or suspension (oil phase) containing the high molecular weight polymer obtained in this manner is added to an aqueous phase to form an O/W emulsion. The solvent in the oil phase is then removed followed by preparation of the microcapsules.

An emulsifier may be added to the aqueous phase. Typical emulsifiers may be used as long as they form a stable O/W emulsion. Examples of these emulsifiers include anionic surfactants (such as sodium oleate, sodium stearate and sodium lauryl sulfate) or non-ionic surfactants such as polyoxyethylene sorbitan fatty acid ester (e.g., Tween 80 or Tween 60, Astra Powder, U.S.A.) and polyoxyethylene castor oil derivative (HCO-30 or HCO-50, Nikko Chemicals), or polyvinyl pyrolidone, polyvinyl alcohol, carboxymethyl cellulose, lecithin and gelatin. One type of these substance may be used or several types may be used in combination.

In addition, microcapsules may also be formed using the coacervation method (Omi, S. and Murakami, A., Powders and Industry, 16, 41, 1984), the in-water drying method (Japanese Unexamined Patent Publication No. 62-201816), the phase separation method (Omi, S., Pharmaceutical Factory, 770, 8, 1986), or the spray drying method (Omi, S., Pharmaceutical Factory, 770, 8, 1986).

Although the above has introduced the example of forming microcapsules, granules, pellets or tablets may also be formed as desired.

The present invention also provides a subcutaneous or intramuscular injection preparation that releases drug continuously at a constant rate, as well as an oral vaccine preparation in which a vaccine according to the present invention is easily incorporated into mesenteric lymph tissue.

EXAMPLES

The present invention will now be further illustrated by, but is by no means limited to, the following Examples. Furthermore, the weight average molecular weights indicated in the following Examples were determined using a polystyrene standard. In addition, measurement of polymerization ratio was performed by NMR spectroscopy.

Example 1

Trans-4-hydroxy-L-proline (3.2 g) and DL-lactic acid (20 g) (mole ratio:10:90) were placed in a 25 ml pear-shaped flask. After adding ion exchange resin (Dowex 50W, Dow Chemicals) (0.4 g) activated with 2N hydrochloric acid and performing nitrogen substitution, the mixture was melted for 2–3 hours at 130°–140° C. under reduced pressure (15 mmHg). The vacuum was raised (1.0 mmHg) and the melt polymerization was performed at about 175° C. for 60 hours. Following the polymerization, the product was dissolved in a small amount of methylene chloride, and after removing the resin with filter paper, the solution was reprecipitated with n-hexane to obtain the copolymer (yield:5.0 g, m.p.:45° C.).

The weight average molecular weight of the resulting copolymer was about 4,000, and the polymerization ratio of trans-4-hydroxy-L-proline and DL-lactic acids was 30:70. The reason for this polymerization ratio differing from the charged mole ratio is because lactide, a dimer of lactic acid, escapes outside the system during polymerization.

Example 2

A solution of trans-4-hydroxy-L-proline (1.31 g) dissolved in distilled water (2.0 ml), and poly(DL-lactic acid) (Wako, molecular weight:20,000) (6.48 g) (mole ratio:trans-4-hydroxy-L-proline:lactic acid=10:90) were placed in a 25 ml pear-shaped flask. After heating for 30 minutes at 110° C. at atmospheric pressure, the mixture was melted at 180° C. under reduced pressure (5 mmHg) to carry out the transesterification (9 hours). After the reaction, the product was dissolved in a small amount of methylene chloride and the solution was reprecipitated with n-hexane to obtain the copolymer (yield:5.6 g, m.p.:55° C.).

The weight average molecular weight of the resulting copolymer was about 12,000, and the polymerization ratio of trans-4-hydroxy-L-proline and DL-lactic acid was 10:90.

Example 3

Trans-4-hydroxy-L-proline (3.8 g) and glycolic acid (20 g) (mole ratio:10:90) were placed in a 25 ml pear-shaped flask. After adding ion exchange resin (Dowex 50W, Dow Chemicals) (0.4 g) activated with 2N hydrochloric acid and performing nitrogen substitution, the mixture was melted for 2–3 hours at 130°–140° C. under reduced pressure (15 mmHg). The vacuum was raised (1.0 mmHg) and the melt polymerization was performed at about 175° C. for 60 hours. Following the polymerization, the product was dissolved in a small amount of methylene chloride, and after removing the resin with filter paper, the solution was reprecipitated with n-hexane to obtain the copolymer (yield:6.5 g).

The weight average molecular weight of the resulting copolymer was about 5,000, and the polymerization ratio of trans-4-hydroxy-L-proline and glycolic acid was 35:65. The reason for this polymerization ratio differing from the charged mole ratio is because glycolide, a dimer of glycolic acid, escapes outside the system during polymerization.

Example 4

Trans-4-hydroxy-L-proline (2.6 g), DL-lactic acids (18.3 g) and glycolic acid (3.0 g) (mole ratio:10:70:20) were placed in a 25 ml pear-shaped flask. After adding ion exchange resin (Dowex 50W, Dow Chemicals) (0.4 g) activated with 2N hydrochloric acid and performing nitrogen substitution, the mixture was melted for 3 hours at 130–140° C. under reduced pressure (15 mmHg). The mixture was additionally heated for 5 hours at 150° C. at 10 mmHg after which the melt polymerization was performed at about 175° C. for 80 hours at high vacuum (1.0 mmHg). Following the polymerization, the product was dissolved in a small amount of methylene chloride, and after removing the resin with filter paper, the solution was reprecipitated with n-hexane to obtain the copolymer (yield:6.5 g).

The weight average molecular weight of the resulting copolymer was about 2,000, and the polymerization ratio of trans-4-hydroxy-L-proline, DL-lactic acids and glycolic acid was 25:60:15. The reason for this polymerization ratio differing from the charged mole ratio is because lactide, a dimer of DL-lactic acids, and glycolide, a dimer of glycolic acid, escape outside the system during polymerization.

Example 5

(1) Trans-4-hydroxy-1-palmitoyl-L-proline methyl ester produced by the method of Langer et al. (Macromolecules, 22, 3250–3255 (1989)) was dissolved in a 2N aqueous solution of NaOH. This solution was stirred for 3 hours at room temperature using a stirrer. After stirring, the solution was neutralized with aqueous hydrochloric acid. After extracting with methylene chloride, the solvent was removed to obtain a white powder of trans-4-hydroxy-1-palmitoyl-L-proline.

(2) This trans-4-hydroxy-1-palmitoyl-L-proline (9.1 g) and DL-lactic acids (20 g) (mole ratio:10:90) were placed in a 25 ml pear-shaped flask. After adding ion exchange resin (Dowex 50W, Dow Chemicals) (0.4 g) activated with 2N hydrochloric acid and performing nitrogen substitution, the mixture was melted for 3 hours at 130°–140° C. under reduced pressure (15 mmHg). The vacuum was raised (1.0 mmHg) and the melt polymerization was performed at about 180° C. for 60 hours. Following the polymerization, the product was dissolved in a small amount of methylene chloride, and after removing the resin with filter paper, the solution was reprecipitated with n-hexane to obtain the copolymer (yield:5.0 g).

The weight average molecular weight of the resulting copolymer was about 7,000, and the polymerization ratio of trans-4-hydroxy-1-palmitoyl-L-proline and DL-lactic acids was 12:88.

Example 6

The trans-4-hydroxy-1-palmitoyl-L-proline (3.6 g) obtained in Example 5, part (1) and poly(DL-lactic acid) (Wako, molecular weight:20,000) (6.48 g) (mole ratio:trans-4-hydroxy-1-palmitoyl-L-proline:poly(DL-lactic acid) = 10:90) were placed in a 25 ml pear-shaped flask. The mixture was melted at 170° C. under reduced pressure (5 mmHg) to carry out the transesterification (3 hours). After the reaction, the product was dissolved in a small amount of methylene chloride and the solution was reprecipitated with n-hexane to obtain the copolymer (yield:6.2).

The weight average molecular weight of the resulting copolymer was about 14,000, and the polymerization ratio of trans-4-hydroxy-1-palmitoyl-L-proline and DL-lactic acid was 10:90.

Example 7

The trans-4-hydroxy-1-palmitoyl-L-proline (10.8 g) obtained in Example 5, part (1) and glycolic acid (20 g) (mole ratio:10:90) were placed in 25 ml pear-shaped flask. After adding ion exchange resin (Dowex 50W, Dow Chemicals) (0.4 g) activated with 2N hydrochloric acid and performing nitrogen substitution, the mixture was melted for 2–3 hours at 130°–140° C. under reduced pressure (15 mmHg). The vacuum was raised (1.0 mmHg) and the melt polymerization was performed at about 180° C. for 60 hours. Following the polymerization, the product was dissolved in a small amount of methylene chloride, and after removing the resin with filter paper, the solution was reprecipitated with n-hexane to obtain the copolymer (yield:3.0 g).

The weight average molecular weight of the resulting copolymer was roughly 6,000, and the polymerization ratio of trans-4-hydroxy-1-palmitoyl-L-proline and glycolic acid was 15:85.

Example 8

The trans-4-hydroxy-1-palmitoyl-L-proline (7.4 g) obtained in Example 5, part (1), DL-lactic acid (12.6 g) and glycolic acid (3.0 g) (mole ratio:10:70:20) were placed in a 25 ml pear-shaped flask and activated with 2N hydrochloric acid. After adding ion exchange resin (Dowex 50W, Dow Chemicals) (0.4 g) and performing nitrogen substitution, the mixture was melted for 3 hours at 130°–140° C. under reduced pressure (15 mmHg). After additionally heating for 5 hours at 150° C. at 10 mmHg, the vacuum was raised (1.0 mmHg) and the melt polymerization was performed at about 180° C. for 80 hours. Following the polymerization, the product was dissolved in a small amount of methylene chloride, and after removing the resin with filter paper, the solution was reprecipitated with n-hexane to obtain the copolymer (yield:15.5 g).

The weight average molecular weight of the resulting copolymer was about 5,000, and the polymerization ratio of trans-4-hydroxy-1-palmitoyl-L-proline, DL-lactic acid and glycolic acid was 15:68:17.

Example 9

N-benzyloxycarbonyl-trans-4-hydroxy-L-proline (6.5 g) and DL-lactic acid (20 g) (mole ratio:10:90) were placed in a 25 ml pear-shaped flask. After adding ion exchange resin (Dowex 50W, Dow Chemicals) (0.4 g) activated with 2N hydrochloric acid and performing nitrogen substitution, the mixture was melted for 2–3 hours at 130°–140° C. under reduced pressure (15 mmHg). The vacuum was raised (10 mmHg) and the melt polymerization was performed at about 175° C. for 60 hours. Following the polymerization, the product was dissolved in a small amount of methylene chloride, and after removing the resin with filter paper, the solution was reprecipitated with n-hexane to obtain the copolymer (yield:20.0 g).

The weight average molecular weight of the resulting copolymer was about 10,000, and the polymerization ratio of N-benzyloxycarbonyl-trans-4-hydroxy-L-proline and DL-lactic acids was 12:88.

Example 10

N-benzyloxycarbonyl-trans-4-hydroxy-L-proline (2.65 g) and poly(DL-lactic acid) (Wako, molecular weight:20,000) (6.48 g) (mole ratio:N-benzyloxycarbonyl-trans-4-hydroxy-L-proline:lactic acid=10:90) were placed in a 25 ml pear-shaped flask. The mixture was melted at 170° C. under reduced pressure (5 mmHg) to carry out the transesterification (3 hours). After the reaction, the product was dissolved in a small amount of methylene chloride and the solution was reprecipitated with n-hexane to obtain the copolymer (yield:6.0 g, m.p.:70° C.).

The weight average molecular weight of the resulting copolymer was about 14,000, and the polymerization ratio of N-benzyloxycarbonyl-trans-4-hydroxy-L-proline and DL-lactic acid was 10:90.

Example 11

N-benzyloxycarbonyl-trans-4-hydroxy-L-proline (8.2 g) and glycolic acid (20 g) (mole ratio:10:90) were placed in a 25 ml pear-shaped flask. After adding ion exchange resin (Dowex 50W, Dow Chemicals) (0.4 g) activated with 2N hydrochloric acid and performing nitrogen substitution, the mixture was melted for 2-3 hours at 130°-140° C. under reduced pressure (15 mmHg). The vacuum was raised (1.0 mmHg) and the melt polymerization was performed at about 175° C. for 60 hours. Following the polymerization, the product was dissolved in a small amount of methylene chloride, and after removing the resin with filter paper, the solution was reprecipitated with n-hexane to obtain the copolymer (yield:3.0 g).

The weight average molecular weight of the resulting copolymer was about 8,000, and the polymerization ratio of N-benzyloxycarbonyl-trans-4-hydroxy-L-proline and glycolic acid was 15:85.

Example 12

N-benzyloxycarbonyl-trans-4-hydroxy-L-proline (5.3 g), DL-lactic acid (12.6 g) and glycolic acid (2.9 g) (mole ratio:10:70:20) were placed in a 25 ml pear-shaped flask. After adding ion exchange resin (Dowex 50W, Dow Chemicals) (0.4 g) activated with 2N hydrochloric acid and performing nitrogen substitution, the mixture was melted for 2-3 hours at 130°-140° C. under reduced pressure (15 mmHg). The vacuum was raised (1.0 mmHg) and the melt polymerization was performed at about 175° C. for 60 hours at high vacuum (1.0 mmHg). Following the polymerization, the product was dissolved in a small amount of methylene chloride, and after removing the resin with filter paper, the solution was reprecipitated with n-hexane to obtain the copolymer (yield:15.0 g).

The weight average molecular weight of the resulting copolymer was about 6,000, and the polymerization ratio of N-benzyloxycarbonyl-trans-4-hydroxy-L-proline, DL-lactic acid and glycolic acid was 15:68:17.

Example 13

(1) Trans-4-hydroxy-1-decanoyl-L-proline methyl ester produced by the method of Langer et al. (Macromolecules, 22, 3250-3255 (1989)) was dissolved in a 2N aqueous solution of sodium hydroxide. This solution was stirred for 3 hours at room temperature using a stirrer. After stirring, the solution was neutralized with aqueous hydrochloric acid. After extracting with methylene chloride, the solvent was removed to obtain a white powder of trans-4-hydroxy-1-decanoyl-L-proline.

(2) This trans-4-hydroxy-1-decanoyl-L-proline (7.1 g) and DL-lactic acid (20 g) (mole ratio:10:90) were placed in a 25 ml pear-shaped flask. After adding ion exchange resin (Dowex 50W, Dow Chemicals) (0.4 g) activated with 2N hydrochloric acid and performing nitrogen substitution, the mixture was melted for 3 hours at 130°-140° C. under reduced pressure (15 mmHg). The vacuum was raised (1.0 mmHg) and the melt polymerization was performed at about 180° C. for 60 hours. Following the polymerization, the product was dissolved in a small amount of methylene chloride, and after removing the resin with filter paper, the solution was reprecipitated with n-hexane to obtain the copolymer (yield:20.0 g).

The weight average molecular weight of the resulting copolymer was about 5,000, and the polymerization ratio of trans-4-hydroxy-1-decanoyl-L-proline and DL-lactic acid was 15:85.

Example 14

N-benzyloxycarbonyl-trans-4-hydroxy-L-proline (6.5 g) and DL-lactic acid (20 g) (mole ratio:10:90) were placed in a 25 ml pear-shaped flask. After adding ion exchange resin (Dowex 50W, Dow Chemicals) (0.4 g) activated with 2N hydrochloric acid and performing nitrogen substitution, the mixture was melted for 3 hours at 130°-140° C. under reduced pressure (15 mmHg). The vacuum was raised (1.0 mmHg) and the weight average molecular weights of the formed N-benzyloxycarbonyl-trans-4-hydroxy-L-proline/DL-lactic acid copolymers were measured after 10, 20, 30, 60, 120 and 240 minutes. Those results are indicated in Table 1.

TABLE 1

| N-benzyloxycarbonyl-trans-4-hydroxy-L-proline/ DL-lactic acid copolymers | | | | | | |
|---|---|---|---|---|---|---|
| Time (min.) | 10 | 20 | 30 | 60 | 120 | 240 |
| Weight average molecular weight of copolymer | about 5,000 | about 6,000 | about 8,000 | about 10,000 | about 17,000 | about 20,000 |

Example 15

(1) Trans-4-hydroxy-1-pivaloyl-L-proline methyl ester produced by the method of Langer et al. (Macromolecules, 22, 3250-3255 (1989)) was dissolved in a 2N aqueous solution of NaOH. This solution was stirred for 3 hours at room temperature using a stirrer. After stirring, the solution was neutralized with aqueous hydrochloric acid. After extracting with methylene chloride, the solvent was distilled off to obtain a white powder of trans-4-hydroxy-1-pivaloyl-L-proline.

(2) This trans-4-hydroxy-1-pivaloyl-L-proline (4.0 g) and DL-lactic acids (20 g) (mole ratio:10:90) were placed in a 25 ml pear-shaped flask. After adding ion exchange resin (Dowex 50W, Dow Chemicals) (0.4 g) activated with 2N hydrochloric acid and performing nitrogen substitution, the mixture was melted for 3 hours at 130°-140° C. under reduced pressure (15 mmHg). The vacuum was raised (1.0 mmHg) and the melt polymerization was performed at about 210° C. for 60 hours. Following the polymerization, the product was dissolved in a small amount of methylene chloride, and after removing the resin with filter paper, the solution was reprecipitated with n-hexane to obtain the copolymer (yield:15.5 g).

The weight average molecular weight of the resulting copolymer was about 5,000, and the polymerization ratio of trans-4-hydroxy-1-pivaloyl-L-proline and DL-lactic acids was 15:85.

Example 16

(1) Trans-4-hydroxy-1-eicosanoyl-L-proline methyl ester produced by the method of Langer et al. (Macromolecules, 22, 3250–3255 (1989)) was dissolved in a 2N aqueous solution of NaOH. This solution was stirred for 3 hours at room temperature using a stirrer. After stirring, the solution was neutralized with aqueous hydrochloric acid. After extracting with methylene chloride, the solvent was distilled off to obtain a white powder of trans-4-hydroxy-1-eicosanoyl-L-proline.

(2) This trans-4-hydroxy-1-eicosanoyl-L-proline (8.8 g) and DL-lactic acids (20 g) (mole ratio:10:90) were placed in a 25 ml pear-shaped flask. After adding ion exchange resin (Dowex 50W, Dow Chemicals) (0.4 g) activated with 2N hydrochloric acid and performing nitrogen substitution, the mixture was melted for 3 hours at 130°–140° C. under reduced pressure (15 mmHg). The vacuum was raised (1.0 mmHg) and the melt polymerization was performed at about 210° C. for 60 hours. Following the polymerization, the product was dissolved in a small amount of methylene chloride, and after removing the resin with filter paper, the solution was reprecipitated with n-hexane to obtain the copolymer (yield:18.5 g).

The weight average molecular weight of the resulting copolymer was about 12,000, and the polymerization ratio of trans-4-hydroxy-1-eicosanoyl-L-proline and DL-lactic acids was 10:90.

Example 17

N-tert-butyloxycarbonyl-trans-4-hydroxy-L-proline (4.5 g) and DL-lactic acid (20 g) (mole ratio:10:90) were placed in a 25 ml pear-shaped flask. After adding ion exchange resin (Dowex 50W, Dow Chemicals) (0.4 g) activated with 2N hydrochloric acid and performing nitrogen substitution, the mixture was melted for 2–3 hours at 130°–140° C. under reduced pressure (15 mmHg). The vacuum was then raised (1.0 mmHg) and the melt polymerization was performed at about 175° C. for 60 hours. Following the polymerization, the product was dissolved in a small amount of methylene chloride, and after removing the resin with filter paper, the solution was reprecipitated with n-hexane to obtain the copolymer (yield:14.5 g).

The weight average molecular weight of the resulting copolymer was about 6,000, and the polymerization ratio of N-tert-butyloxycarbonyl-trans-4-hydroxy-L-proline and DL-lactic acid was 15:85.

Example 18

The trans-4-hydroxy-L-proline/DL-lactic acid copolymer (abbreviated as HyP-LA) (molecular weight:about 4,000) (1 g) prepared in Example 1 was dissolved in a small amount of methylene chloride and placed in a 5 ml syringe. This was then expelled onto a glass plate from a diameter 1.5 mm nozzle. The glass plate was then dried in a dessicator for 24 hours. Rod-shaped pellets having a diameter of about 1 mm were obtained by cutting the dried copolymer to appropriate lengths. The pellets were implanted beneath the skin on the backs of rats (4-week-old, male Wistar rats). Incisions were made after 1, 2 and 4 weeks to remove the surrounding tissue. When the tissue specimens were observed with a light microscope following HE staining, there were no abnormalities observed.

Example 19

With the exception of using the trans-4-hydroxy-1-palmitoyl-L-proline/glycolic acid copolymer (abbreviated as PalHyP-GA) (molecular weight:about 6,000) (1 g) prepared in Example 7 for the copolymer in Example 18, rod-shaped pellets having a diameter of about 1 mm were obtained in the same manner as Example 18. The pellets were implanted beneath the skin on the backs of rats (4-week-old, male Wistar rats). Incisions were made after 1, 2 and 4 weeks to remove the surrounding tissue. When the tissue specimens were observed with a light microscope following HE staining, there were no abnormalities observed.

Example 20

With the exception of using the N-benzyloxycarbonyl-trans-4-hydroxy-L-proline/DL-lactic acid/glycolic acid copolymer (abbreviated as Z-HyP-LGA) (molecular weight:about 6,000) (1 g) prepared in Example 12 for the copolymer in Example 18, rod-shaped pellets having a diameter of about 1 mm were obtained in the same manner as Example 18. The pellets were implanted beneath the skin on the backs of rats (4-week-old, male Wistar rats). Incisions were made after 1, 2 and 4 weeks to remove the surrounding tissue. When the tissue specimens were observed with a light microscope following HE staining, there were no abnormalities observed.

Example 21

In vivo solubility of the copolymer pellets used in Examples 18–20 was evaluated by implanting the pellets beneath the skin on the backs of rats (4-week-old, male Wistar rats), making incisions after 1, 2 and 4 weeks to remove the pellets and weighing each of the pellets (solubility, %).

Those results are shown in FIG. 1. In FIG. 1, triangles indicate the results for HyP-LA, circles indicate the results for PalHyP-GA, and squares indicate the results for Z-HyP-LGA.

Example 22

Two types of insulin microcapsules were produced using the trans-4-hydroxy-L-proline/glycolic acid copolymer (polymerization ratio:35:65, molecular weight:about 5,000) obtained in Example 3 and polyglycolic acid (molecular weight:about 5,000).

First of all, insulin (bovine, Sigma, I-5500) (100 mg) was dissolved in 0.1 N hydrochloric acid (2 ml) followed by neutralization to pH 7.0 with 1 N aqueous sodium hydroxide to obtain an insulin solution of about 50 mg/ml. A solution of 2 g of the above-mentioned copolymer dissolved in methylene chloride (7 ml) and Tween 80 (Astra Powder) (1 ml) was then added to this insulin solution followed by addition to an aqueous solution of polyvinyl alcohol (PVA) (200 ml). A W/O/W emulsion was then formed by mixing at 2,000 rpm using a turbine homogenizer. After the internal W/O emulsion was solidified by evaporation of methylene chloride while stirring the W/O/W emulsion liquid, this emulsion was collected by filtration. This was then again dispersed in 0.02 N hydrochloric acid and then distilled water followed by washing and filtration of the free drug.

A powder was obtained after completely removing solvent and water by freeze-drying the collected microcapsules. The average diameter of the resulting powder-form products was about 10–200 μm.

The results of in vitro insulin release test of the microcapsules obtained by the method described above at 37° C. and in a phosphate buffer having a pH of 7.0 are shown in Table 2.

TABLE 2

| In Vitro Release Properties (Percentage Remaining in Microcapsules (%)) | | | | |
|---|---|---|---|---|
| Microcapsule Material | 1 Day | 3 Days | 1 Week | 2 Weeks |
| Trans-4-hydroxy-L-proline/glycolic acid copolymer | 90 | 75 | 50 | 10 |
| Polyglycolic acid | 70 | 45 | 20 | 0 |

Based on the results of Table 2, although a large initial release of insulin is observed in the case of polyglycolic acid, in the case of the trans-4-hydroxy-L-proline/glycolic acid copolymer of the present invention, microcapsules having suppressed initial burst phenomenon and favorable release properties were obtained.

Example 23

Two types of insulin microcapsules were produced using the trans-4-hydroxy-1-palmitoyl-L-proline/DL-lactic acid copolymer (polymerization ratio:12:88, molecular weight:about 7,000) obtained in Example 5 and poly-DL-lactic acid (molecular weight:10,000). Production was performed following the method of Example 22. The average diameter of the resulting powder-form products was roughly 10–200 μm.

The results of in vitro insulin release test of the resulting microcapsules at 37° C. and in a phosphate buffer having a pH of 7.0 are indicated in Table 3.

TABLE 3

| In Vitro Release Properties (Percentage Remaining in Microcapsules (%)) | | | | |
|---|---|---|---|---|
| Microcapsule Material | 1 Day | 3 Days | 1 Week | 2 Weeks |
| Trans-4-hydroxy-1-palmitoyl-L-proline/DL-lactic acid copolymer | 90 | 80 | 55 | 25 |
| Poly-DL-lactic acid | 90 | 85 | 80 | 75 |

In contrast to insulin release being extremely slow in the case of poly-DL-lactic acid, microcapsules having suppressed initial burst phenomenon and favorable release properties were obtained in the case of the trans-4-hydroxy-1-palmitoyl-L-proline/DL-lactic acid copolymer of the present invention.

Example 24

Two types of insulin microcapsules were produced using the N-benzyloxycarbonyl-trans-4-hydroxy-L-proline/DL-lactic acid/glycolic acid copolymer (polymerization ratio:15:68:17, molecular weight:about 6,000) obtained in Example 12 and poly(DL-lactic-co-glycolic)acid (polymerization ratio:75:25, molecular weight:about 5,000). Production was performed following the method of Example 24. The average diameter of the resulting powder-form products was about 10–200 μm.

The results of in vitro insulin release test of the resulting microcapsules at 37° C. and in a phosphate buffer having a pH of 7.0 are shown in Table 4.

TABLE 4

| In Vitro Release Properties (Percentage Remaining in Microcapsules (%)) | | | | |
|---|---|---|---|---|
| Microcapsule Material | 1 Day | 3 Days | 1 Week | 2 Weeks |
| N-benzyloxycarbonyl-trans-4-hydroxy-L-proline/DL-lactic acid/glycolic acid copolymer | 70 | 50 | 10 | 0 |
| Poly-DL-lactic acid | 50 | 20 | 0 | 0 |

Based on the results of Table 4, although a large initial release of insulin is observed in the case of poly(DL-lactic-co-glycolic)acid, in the case of the N-benzyloxycarbonyl-trans-4-hydroxy-L-proline/DL-lactic acid/glycolic acid copolymer of the present invention, microcapsules having suppressed initial burst phenomenon and favorable release properties were obtained.

Example 25

Four types of trans-4-hydroxy-1-palmitoyl-L-proline/DL-lactic acid copolymers (molecular weight: about 7,000) having polymerization ratios of 5:95, 12:88, 20:80 and 35:65 were produced according to the method of Example 5. Insulin microcapsules were then produced according to the method of Example 24 using these copolymers. The average diameter of the resulting powder-form products was about 10–200 μm.

The results of in vitro insulin release test of the resulting microcapsules at 37° C. and in a phosphate buffer having a pH of 7.0 are shown in Table 5.

TABLE 5

| In Vitro Release Properties (Percentage Remaining in Microcapsules (%)) | | | | |
|---|---|---|---|---|
| Polymerization ratios of trans-4-hydroxy-1-palmitoyl-L-proline/DL lactic acid copolymers | 1 Day | 3 Days | 1 Week | 2 Weeks |
| 5:95 | 90 | 85 | 70 | 50 |
| 12:88 | 90 | 80 | 55 | 25 |
| 20:80 | 85 | 75 | 45 | 10 |
| 35:65 | 80 | 60 | 20 | 10 |

It can be determined from Table 5 that as the proportion of trans-4-hydroxy-1-palmitoyl-L-proline of the copolymer increases, the rate of insulin release also increases.

Example 26

A thyroid hormone releasing hormone (TRH) continuous injection preparation was produced using the trans-4-hydroxy-1-palmitoyl-L-proline/DL-lactic acid copolymer obtained in Example 5.

First of all, TRH acetate (100 mg) was dissolved in water (2 ml). A solution of the above-mentioned copolymer (2 g) dissolved in methylene chloride (7 ml) and Tween 80 (1 ml) was added to the above solution, followed by ultrasonic mixing (2 minutes) to prepare a W/O emulsion. This emulsion was added to 200 ml of a 3% aqueous solution of polyvinyl alcohol followed by mixing for 2 minutes at 2,000 rpm using a turbine homogenizer to form a W/O/W emulsion. After the internal W/O emulsion was solidified by evaporation of methylene chloride while stirring the W/O/W emulsion liquid, this emulsion was collected by filtration. This was then again dispersed in distilled water, followed by washing and filtration of the free drug. A powder was obtained after completely removing solvent and water by freeze-drying the collected microcapsules. The average diameter of the resulting powder-form products was about 10–200 μm.

This powder (100 mg) was then suspended in D-mannitol (75 mg) functioning as an isotonic agent, carboxymethyl cellulose (7.5 mg) functioning as a dispersant, Tween 80 (Astra Powder) (1.5 mg) and distilled water for injection to obtain a continuous injection preparation.

Example 27

A salmon calcitonine (SCT) continuous injection preparation was produced using the trans-4-hydroxy-1-palmitoyl-L-proline/DL-lactic acid copolymer obtained in Example 5.

First of all, SCT (3.2 mg, 16000 unit) was dissolved in water (2 ml). A solution of the above-mentioned copolymer (2 g) dissolved in methylene chloride (7 ml) and Tween 80 (1 ml) was added to the above solution, followed by ultrasonic mixing (2 minutes) to prepare a W/O emulsion. This emulsion was added to 200 ml of a 3% aqueous solution of polyvinyl alcohol, followed by mixing for 2 minutes at 2,000 rpm using a turbine homogenizer to form a W/O/W emulsion. After the internal W/O emulsion was solidified by evaporation of methylene chloride while stirring the W/O/W emulsion liquid, this emulsion was collected by filtration. This was then again dispersed in distilled water, followed by washing and filtration of the free drug. A powder was obtained after completely removing solvent and water by freeze-drying the collected microcapsules. The average diameter of the resulting powder-form products was about 10–200 μm.

This powder (100 mg) was then suspended in D-mannitol (75 mg) functioning as an isotonic agent, carboxymethyl cellulose (7.5 mg) functioning as a dispersant, Tween 80 (Astra Powder) (1.5 mg) and distilled water for injection to obtain a continuous injection preparation.

Example 28

A pertussis vaccine oral preparation was produced using the trans-4-hydroxy-1-palmitoyl-L-proline/DL-lactic acid copolymer obtained in Example 5.

First of all, pertussis vaccine (pertussis toxin (PT)) (50 mg) and filamentous hemagglutinin (FHA) (50 mg) were dispersed in a solution of the above-mentioned copolymer (2 g) dissolved in methylene chloride (7 ml) and Tween 80 (Astra Powder) (1 ml). This was added to a 3% aqueous solution of polyvinyl alcohol (200 ml) followed by mixing for 2 minutes at 10,000 rpm using a turbine homogenizer to prepare an O/W emulsion. After solidifying the oil phase by evaporation of methylene chloride while stirring the O/W emulsion liquid, it was collected by filtration. After completely removing solvent and water by freeze-drying, the collected microcapsules were obtained in the form of a powder. The average diameter of the resulting powder-form products was about 1–10 μm.

This powder (100 mg) was then suspended in carboxymethyl cellulose (7.5 mg) functioning as a dispersant, Tween 80 (Astra Powder) (1.5 mg) and distilled water to obtain a pertussis vaccine preparation for both oral and nasal administration.

We claim:

1. A biodegradable copolymer having the constituent units represented by the structures (I) and (II):

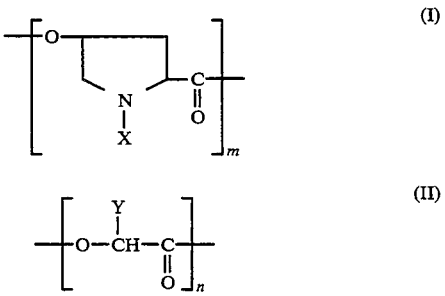

wherein X represents a hydrogen atom, an acyl group having the formula RCO— where R is a hydrocarbon group having 1 to 20 carbon atoms, an alkoxy group having to 20 carbon atoms, and Y represents a hydrogen atom or an alkyl group having 1 to 8 carbon atoms, and m and n are independently integers of 1 or more, m+n is at least 10, and m/(m+n) is at least 0.01.

2. A copolymer as claimed in claim 1, wherein R in the structure (I) is an alkyl group having 1 to 20 carbon atoms.

3. A copolymer as claimed in claim 1, wherein R in the structure (I) is an aliphatic alkoxy group having 4 to 8 carbon atoms or an aromatic alkoxy group having 7 to 9 carbon atoms.

4. A copolymer as claimed in claim 1, wherein Y in the structure (II) is a hydrogen atom or a methyl group.

* * * * *